United States Patent [19]

Danis et al.

[11] Patent Number: 4,921,481
[45] Date of Patent: May 1, 1990

[54] ENTERAL FEEDING SYSTEM UTILIZING GASTROINTESTINAL MYOELECTROGRAPHY

[75] Inventors: Roger G. Danis, Westerville; Ronald M. Isaac, Worthington; Harry A. Puryear, Jr., Dublin, all of Ohio

[73] Assignee: Abbott Laboratories, Abbott Park, Ill.

[21] Appl. No.: 172,055

[22] Filed: Mar. 23, 1988

[51] Int. Cl.⁵ .................................. A61M 31/00
[52] U.S. Cl. .............................. 604/67; 128/642
[58] Field of Search .............. 604/67, 65, 66, 50, 604/245, 270; 128/642, 733, 780, 784

[56] References Cited

U.S. PATENT DOCUMENTS

| | | | |
|---|---|---|---|
| 2,729,211 | 1/1956 | Peter | 128/642 |
| 3,411,507 | 11/1968 | Wingrove | 128/784 |
| 3,480,003 | 11/1969 | Crites | 128/780 |
| 3,860,000 | 1/1975 | Wootten et al. | 604/66 |
| 4,213,466 | 7/1980 | Stulen | 128/733 |
| 4,381,011 | 4/1983 | Somers | 604/280 |
| 4,476,872 | 10/1984 | Perlin | 128/642 |
| 4,683,890 | 8/1987 | Hewson | 128/419 PG |
| 4,769,014 | 9/1988 | Russo | 604/270 |

FOREIGN PATENT DOCUMENTS 2530462  1/1984  France ........................ 604/67

*Primary Examiner*—Lee S. Cohen
*Assistant Examiner*—Kennedy J. Schaetale
*Attorney, Agent, or Firm*—Donald O. Nickey; Edward H. Gorman, Jr.; Martin L. Katz

[57] ABSTRACT

An improved system for initially positioning and for continuous or intermittent monitoring of the location of the distal end of a feeding tube in a patient's gastrointestinal tract and for selectively controlling a feeding device associated therewith by detecting and processing myoelectric signals unique to different areas of the gastrointestinal tract, such signals being detected by electrodes carried by the distal end of the feeding tube and transmitted by leads extending through the feeding tube to a monitor.

18 Claims, 2 Drawing Sheets

ENTERAL FEEDING SYSTEM UTILIZING GASTROINTESTINAL MYOELECTROGRAPHY

BACKGROUND OF THE INVENTION

In many patients, gastrointestinal feeding is the preferred route of nutrient delivery with either the stomach or the upper portion of the small intestine being the two areas of major importance. Proper positioning of the feeding end of an enteral feeding tube in the desired area of the gastrointestinal tract has always been a problem. Even after proper positioning of the feeding end of a feeding tube in either the stomach or the small intestine, it is possible that the feeding end of the tube may unknowingly migrate from the selected area whereupon the patient may be subject to a risky feeding situation. A common method of initially positioning and then monitoring the proper positioning of the feeding end of such a gastrointestinal feeding tube has been by the use of X-ray. To repeatedly verify proper placement in this manner is not only cumbersome and expensive, but it also subjects the patient to unnecessary X-ray exposure.

One attempt to improve this situation is disclosed in U.S. Pat. No. 4,381,011 to Somers, dated April 26, 1983, wherein the pH or acidity of certain portions of a gastrointestinal tract are monitored by a pH measuring device positioned on the end of a feeding tube. However, as the pH may vary as the feeding process proceeds and may also be affected by extraneous factors, the monitored results may be seriously deficient as to the desired accuracy thereof. X-rays, etc. would probably be necessary for back-up purposes.

Further as to Somers and applicants' disclosure herein, the basic functions of the gastrointestinal system, the primary organs being the esophagus, the stomach, and the small intestine, are to mechanically transport foodstuff, chemically break down complex food ingredients, and to absorb processed foodstuff into the blood. Each of the noted primary organs possesses a muscle coat which contracts and propels the foodstuff along the system (peristalsis). This muscle contraction is controlled by nerve tissue via the movement of calcium and other ions from inside the cell to outside the cell and vice versa. This effect begins at a specific anatomical region called a pacemaker and propagates through the muscle mass of that organ. A complete cycle consists of depolarization, hyperpolarization and repolarization of the cell wall. The ion concentrations undergo increases and decreases during the cycle with each of the foregoing organs being characterized by its own cyclic frequency. This ion movement causes a chemical interaction at the surface of applicants' feeding tube electrodes whereby electrical potentials are created, voltage being the unit of measure for the difference between the two sources of electrical potential, applicants' electrodes. Applicants' feeding tube electrodes therefore detect any cyclic change in electrical voltage at their location in a patient's gastrointestinal tract.

Somers, on the other hand, depends on the digestive activities in the stomach where foodstuff is chemically broken down by pepsin and hydrochloric acid. The acid is produced in the stomach which is, therefore, normally a zone of high acid concentration relative to the esophagus and the small intestine due to the esophageal and pyloric sphincters at the entrance to and exit from the stomach, respectively. Acidity is measured in pH units which is the concentration of the hydrogen ion. Thus, a pH electrode undergoes a reaction which is dependent on the concentration of hydrogen ions adjacent thereto, which reaction produces an electrical potential. However, in pH systems the second potential source needed to measure a voltage must be provided by a reference electrode. It is obvious, therefore, that the pH system of Somers is affected to a much greater degree by gastrointestinal contents than is applicants' myoelectrography system disclosed herein, which myoelectrography system thus provides much more accurate results.

SUMMARY OF THE INVENTION

The present invention is directed to an apparatus which aids in initially positioning a feeding tube in a desired location in a patient's gastrointestinal tract and which provides continuous assurance that nutrients are being delivered into that preselected area. This apparatus thus provides a new advanced level of clinical patient care. If an automatic feeding system, such as a pump or a flow-regulating clamp, is operably connected to the feeding tube of the present invention, any migratory movement of the feeding end thereof out of its desired position in the gastrointestinal tract is automatically detected and monitored, whereupon the feeding system is automatically shut down until the feeding end of the feeding tube has been repositioned to its proper location in the patient's gastrointestinal tract.

It has been determined that different areas of a human being's anatomy including the gastrointestinal tract are characterized by electrical signals of different frequencies generated by muscle activity at such areas, such muscle-generated signals being known as myoelectric signals. For instance, in normal human beings, it is known that myoelectric signals originate in the stomach area at a rate of three per minute and in the duodenum of the small intestine at a rate of eleven per minute. Other areas of the gastrointestinal tract, such as the esophagus, the distal-most post-pyloric portion of the small intestine, and the colon, would produce different frequency signals. Continuous detection and monitoring of these myoelectric depolarization signals at the distal feeding end of a feeding tube, a technology known as gastrointestinal myoelectrography, provides immediate notification of changes in the positioning thereof. Further, gastrointestinal myoelectrography may be able to determine changes in the functioning of any of these areas of the gastrointestinal tract by detecting minor variations in the aforesaid depolarization signal frequencies, for instance, to automatically determine and control the rate of operation of a feeding system and also to automatically introduce suitable selected nutrients; to automatically monitor post-surgical patients for return of gastrointestinal motility; and/or to differentiate between absorption disorders and rhythm disorders during diagnostic procedures.

The present invention is directed to a feeding tube which is provided at its distal end, the feeding end thereof, with one or more electrodes which detect such myoelectric signals. The invention may also be characterized by an amplifier/filter module to which the detected signals are fed, by a monitor which receives the signals from the module, and by a feeding system which may be controlled by the monitor.

An object of the present invention is to provide a new and improved system for initially positioning and then monitoring the position of a feeding tube in a patient's gastrointestinal tract by detecting and monitoring myoelectric signals generated therein, which signals may also be used to control an enteral nutrient feeding system.

Another object of the present invention is to provide a new and improved feeding tube of the type having a bolus at its distal end and a Y-connector at its outer end, wherein the bolus has one or more spaced apart electrodes provided thereon with leads from the electrodes passing through the feeding tube to a monitor.

DESCRIPTION OF THE PREFERRED EMBODIMENT

Figure 1:
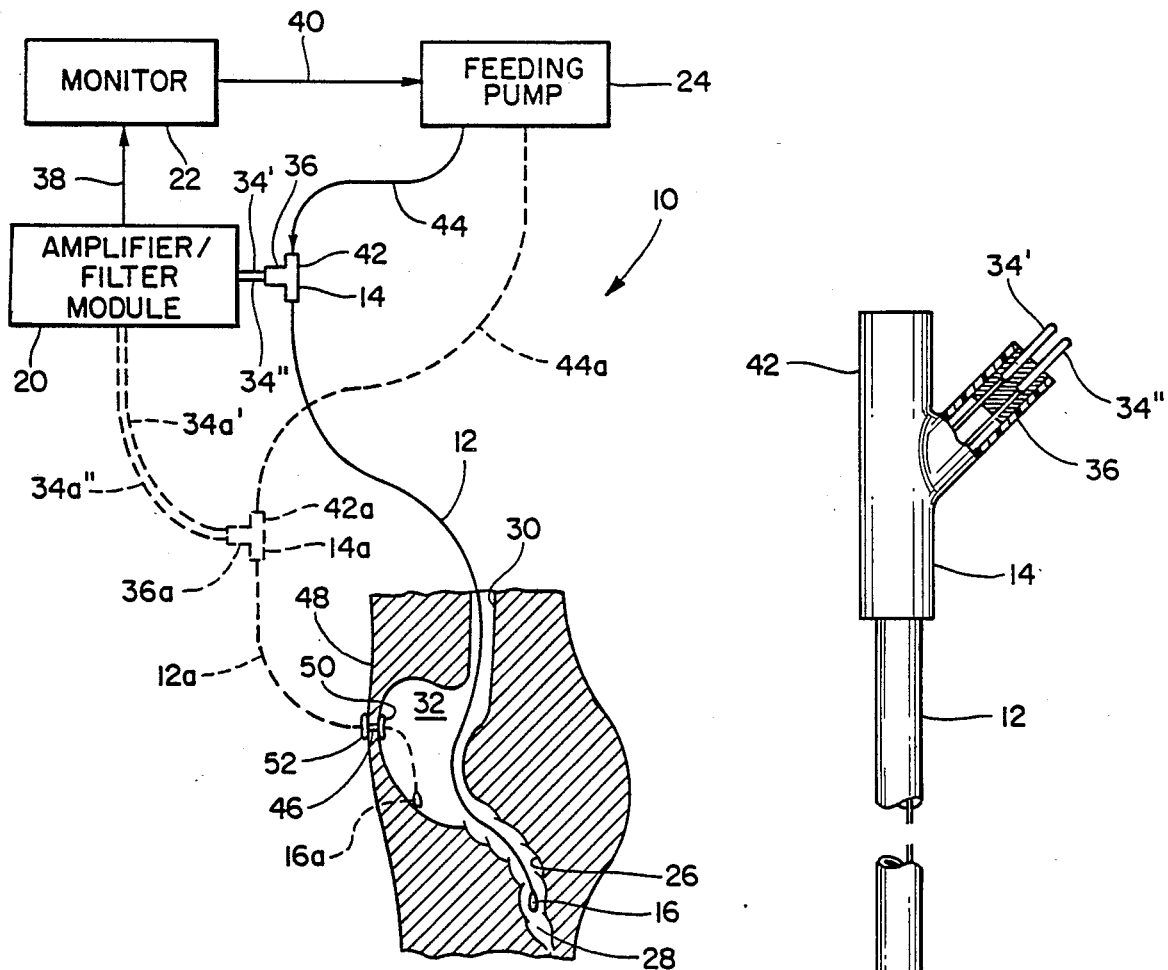
FIG. 1 is a diagrammatic view of a locating/feeding system embodying the invention with a nasal-enteral feeding tube having a bolus located in a patient's small intestine being shown in full line and with an abdominal stoma feeding tube having a bolus located in the stomach being shown in broken line.

Referring now to the drawings, two possible forms of a gastrointestinal locating/feeding system 10 embodying the invention for the feeding of liquid nutrients into preselected areas of the gastrointestinal tract are shown in FIG. 1. The system 10 includes an elongated, flexible, feeding tube 12,12a having a suitable Y-connector 14,14a provided on its proximal end and a bolus 16,16a provided at its distal feeding end, which bolus 16,16a is provided with voltage-sensing (myoelectric signals) electrodes 18' and 18'' (FIGS. 2 and 4); a module 20 for amplifying the detected myoelectric signals and for filtering out undesired frequencies; a monitor 22 capable of processing the detected signals; and, in certain instances, a controllable feeding device 24 such as an infusion pump or a flow-regulating clamp.

Figure 5:
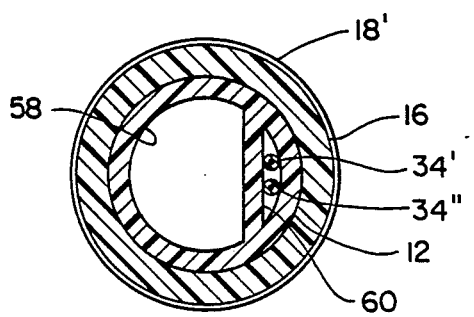
FIG. 5 is an enlarged transverse sectional view taken generally along line 5—5 of FIG. 4.

Two of several possible forms of the system 10 are illustrated in FIG. 1. A nasal-enteral feeding arrangement into the upper portion or duodenum 26 of a patient's small intestine 28, as shown in full line, is characterized by the feeding tube 12 which extends through the patient's esophagus 30 and through the patient's stomach 32 with the bolus 16 being positioned in the patient's duodenum 26. The Y-connector 14 is provided on the proximal end of the feeding tube 12 and sheathed leads 34' and 34'', which are connected to the electrodes 18' and 18'' by a connector 19' and by a connector for lead 34'' which is not visible in FIG. 2, extend through the feeding tube 12 (FIGS. 2 and 3) and out of the Y-connector 14 through an arm 36 thereof for connection to the amplifier/filter module 20. As is best shown in FIG. 5, a separate passage or lumen 60 may be provided in the feeding tube 12,12a for the electrode leads 34' and 34''. An abdominal stoma feeding arrangement passing transcutaneously into the patient's stomach 32, as shown in broken line in FIG. 1, is characterized by the feeding tube 12a which extends through a stoma 46 provided in the abdominal wall 48 with the bolus 16a being positioned in the stomach 32. Adjustable retaining members 50 and 52 are provided on the feeding tube 12a at internal and external ends of the stoma 46, respectively, as an aid in preventing undesirable movement of the feeding tube 12a relative thereto. The Y-connector 14a is provided on the proximal end of the feeding tube 12a and sheathed electrode leads 34a' and 34a'' extend outwardly of the Y-connector 12a through an arm 36a thereof for connection to the amplifier/filter module 20.

Figure 3:
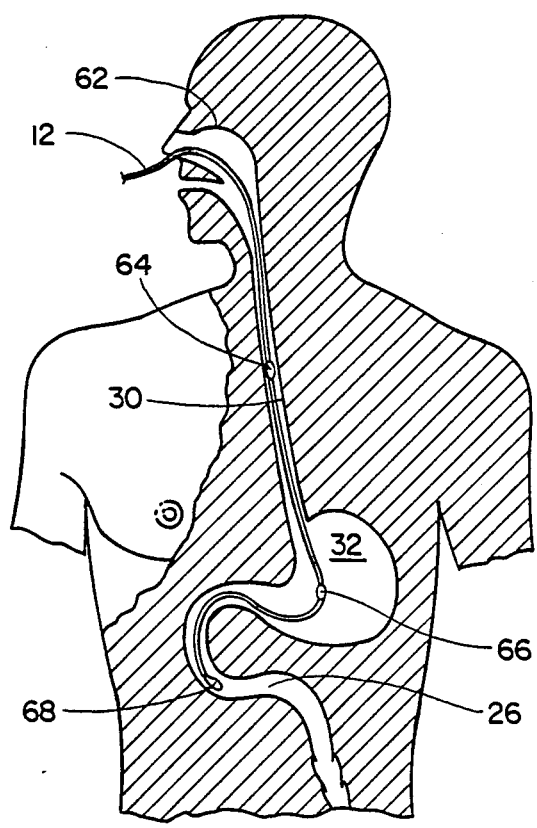
FIG. 3 is a diagrammatic view of a nasal-catheter arrangement having three electrode means positioned respectively in the esophagus, the stomach, and the small intestine.

Although not shown in the drawings, it is noted that the bolus 16 of the nasal-enteral feeding tube 12 may, if desired, be positioned in the stomach 32, the remaining small bowel, or the colon (not shown) if the myoelectric signals of these areas of a patient's gastrointestinal tract are to be monitored. Likewise, it is noted that the bolus 16a of the abdominal stoma feeding tube 12a may, if desired, be positioned in the duodenum 26 or even in the patient's remaining small bowel or colon. As illustrated in FIG. 3, there may be instances where it is desirable for diagnostic or treatment purposes to have a feeding tube 12 which extends through a patient's nasal passage 62 and which has three spaced electrode means provided thereon, an esophageal electrode means 64, a stomach electrode means 66, and a small bowel electrode means 68.

The amplifier/filter module 20, which filters out all frequencies outside the range of physiological interest as well as 60 hertz noise, will amplify the detected signal to a magnitude acceptable to the monitor 22 and will also provide impedance matching between the feeding tube electrodes 18' and 18'' and the monitor 22. The module 20 is suitably connected to the monitor 22, as at 38 and the monitor 22 may be suitably connected to the feeding device 24, as at 40. The monitor 22 is an electronic device which is adapted to process the detected electrophysiological or myoelectric signals received from the module 20 in such a way that the unique properties of the various segments of the enteral tract's electrical activity can be readily identified. Once the parameters of the signals are determined, they may be compared to selected standards by the programming of the monitor 22. The monitor program will also contain a logic path such that the results of the comparison may be used to control the feeding device 24 whereby the feeding device 24 may be directed to maintain its current feeding rate setting or to increase/decrease the rate of nutrient feeding or even to select a different nutrient. This unique system 10 thus provides a solution to the problem of overloading a patient's gastrointestinal tract. Feeding is normally started at a low rate of infusion which is periodically increased until the patient's nutrient needs are met or the patient exhibits discomfort or other symptoms. However, this system 10 allows digestive problems to be recognized and prevented by regulating the rate of feeding prior to gastric overload and the onset of more harmful physical symptoms such as cramps, nausea, vomiting, diarrhea. gastric reflux, or aspiration pneumonia. The feeding device 24 may be connected to another arm 42,42a of the Y-connector 14,14a by a tube set 44,44a.

Another major problem of gastrointestinal feeding is that of initially positioning the feeding end of the tube 12,12a the bolus 16,16a at the desired location in the gastrointestinal tract during the intubation process and later verifying that the proper placement still exists.

Past and current practice is to use X-rays, aspiration, and ascultation to locate the bolus, all of which have serious drawbacks. The present system 10 provides a direct, continuous, and reliable method of overcoming this problem as the monitor 22 may be programmed to not only regulate a feeding rate but also to sound an alarm or otherwise alert an observer while it may also simultaneously cease the feeding should the bolus 16,16a migrate away from its proper feeding position or if a malady such as dysrhythmia occurs. The monitor 22 may also possess display and storage devices such as a CRT display, a chart recorder and/or a magnetic tape recorder, whereby to provide a record of the detected signals.

Figure 2:
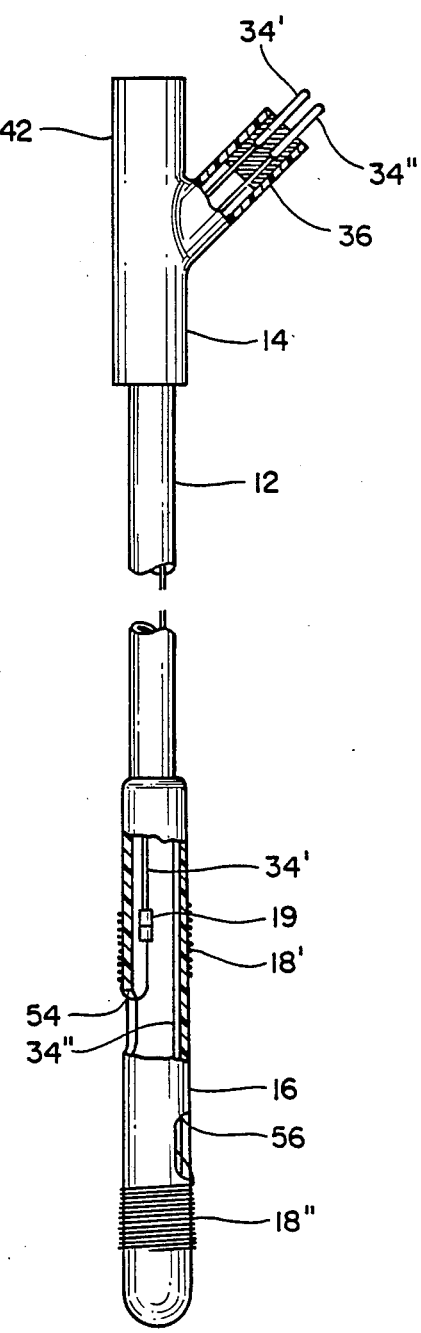
FIG. 2 is an enlarged, front elevational view, partially in longitudinal section, of a feeding tube/bolus/Y-connector assembly embodying the invention.
Figure 4:
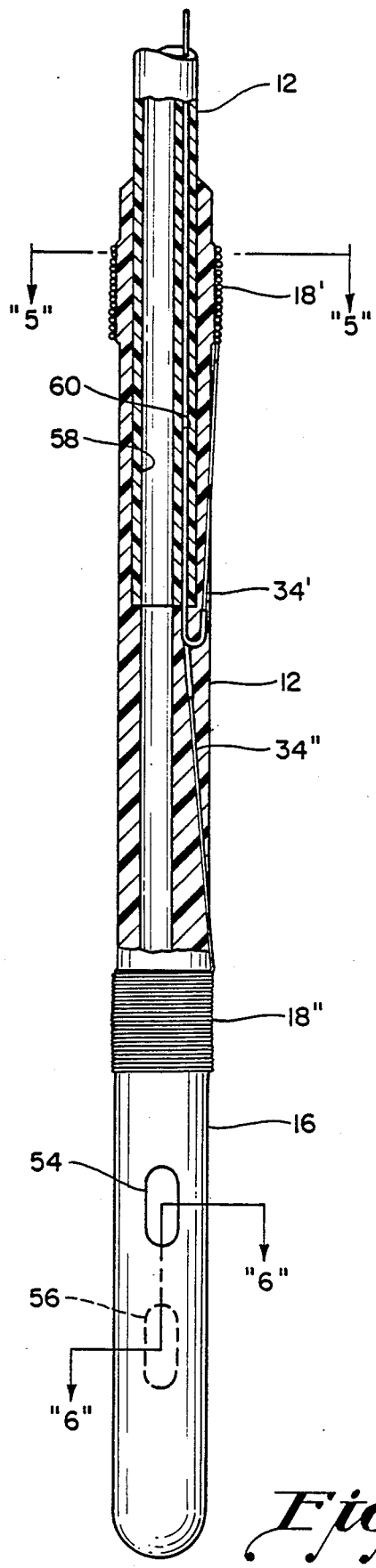
FIG. 4 is a further enlarged, side elevational view, partially in longitudinal section, of a bolus having a modified placement of electrodes thereon.
Figure 6:
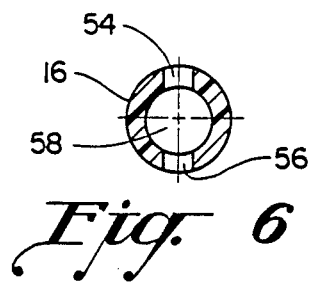
FIG. 6 is a transverse sectional view taken generally along line 6—6 of FIG. 4.

With reference to FIGS. 2 and 4, it is noted that the electrodes 18' and 18" of the preferred embodiment are in the form of coils of fine metal wire wrapped around the bolus 16 in spaced-apart relationship and adjacent to nutrient exit ports 54 and 56 provided in the bolus 16. The metal wire for the electrodes 18' and 18" should have good electrical conductivity such as is provided by gold, silver and platinum wire, for instance. Another suitable wound-coil electrode would be a silver/silver chloride electrode formed of silver wire coated with a chloride salt of silver. The wound coil configuration presents a conducting surface all around the circumference of the bolus 16 while maintaining flexibility in that the individual coils can deform and deflect in conformance with changes in the shape of the bolus 16, as during the intubation process.

However, it is noted that many other forms of electrodes besides wound-coil electrodes may be used in the gastrointestinal locating/feeding system 10 of the present invention.

The multiple lumen feeding tube arrangement, as is best illustrated in FIGS. 4 and 5, provides means for detecting myoelectric signals in desired locations in a patient's gastrointestinal tract while simultaneously introducing liquid nutrients at the site of detection. Two pathways are provided in the tube 12, a fluid channel 58 communicating throughout the length of the tube 12 and providing a means for the liquid nutrient to move from its source, the feeding device 24, to the bolus nutrient exit ports 54 and 56 and a separate channel or lumen 60 separate from the fluid path 58 but still inside the tube 12 and providing a means for electrical communication between the electrodes 18' and 18" and the module 20 by passage of the sheathed leads 34' and 34" therethrough.

While there has been shown and described several possible embodiments of the invention, it will be obvious to those skilled in the art that changes and modifications may be made without departing from the invention, and it is intended by the appended claims to cover all such changes and modifications as fall within the true spirit and scope of the invention.

We claim:

1. In a feeding tube of the type having distal and proximal ends and a nutrient exit port for supplying nutrient at its distal end, apparatus adjacent said nutrient exit port for determining the location thereof in and/or changes in the functioning of different areas of the gastrointestinal tract of a patient, said apparatus comprising, means provided on said distal end for detecting myoelectric signals developed by the surrounding area of the astrointestinal tract in which it is located, said detecting means comprises one or more electrodes around spaced apart portions of said distal end, and means for monitoring said signals.

2. The apparatus as recited in claim 1 wherein said electrodes are formed of gold wire.

3. The apparatus as recited in claim 1 wherein said electrodes are formed of silver wire.

4. The apparatus as recited in claim 1 wherein said electrodes are formed of platinum wire.

5. The apparatus as recited in claim 1 wherein said electrodes are formed of silver/silver chloride wire.

6. In combination with a nasal-enteral feeding tube comprising an elongated tubular flexible main portion with distal and proximal ends having a longitudinally extending lumen therein and an exit port means for supplying nutrients at said distal end, apparatus for detecting and monitoring myoelectric signals originating in various regions of a patient's gastrointestinal tract such as the esophagus, the stomach, and the small intestine, said apparatus comprising, a plurality of electrode means provided on portions of said feeding tube disposed in the esophagus, the stomach, and the small intestine for detecting myoelectric signals developed in said esophagus, said stomach, and said small intestine, said electrode means are in the form of wire coils wound around said feeding tube, and means for monitoring said signals.

7. The apparatus as recited in claim 6 wherein leads extend from said electrode means through said feeding tube to said monitoring means.

8. In a feeding tube of the type having distal and proximal ends and a bolus at its distal end, said bolus having an exit port means for supplying nutrients, apparatus for determining the location of said bolus in different areas of a patient's gastrointestinal tract, said apparatus comprising, electrode means provided on said bolus for detecting myoelectric signals developed by the surrounding area of the gastrointestinal tract in which it is located, said electrode means comprises one or more electrodes around spaced apart areas of said bolus, and means for monitoring said signals whereby to determine the location of said bolus in the patient's gastrointestinal tract.

9. The apparatus as recited in claim 8 wherein said electrodes are formed of gold wire.

10. The apparatus as recited in claim 8 wherein said electrodes are formed of silver wire.

11. The apparatus as recited in claim 8 wherein said electrodes are formed of platinum wire.

12. The apparatus as recited in claim 8 wherein said electrodes are formed of silver/silver chloride wire.

13. In a feeding tube of the type having distal and proximal ends, a bolus at its distal end with an exit port means for supplying nutrients and a Y-connector at its proximal end, apparatus for determining changes in the functioning of different areas of a patient's gastrointestinal tract, said apparatus comprising, electrode means provided on said bolus for detecting myoelectric signals developed by the surrounding area of the gastrointestinal tract in which it is located, said electrode means comprises one or more electrodes around spaced apart areas of said bolus, a feeding system operably connected to said Y-connector for delivering nourishment through said feeding tube and said bolus to the patient, and means for monitoring said signals and for selectively controlling said feeding system.

14. The apparatus as received in claim 13 wherein said electrodes are formed of gold wire.

15. Apparatus as recited in claim 13 wherein said electrodes are formed of silver wire.

16. Apparatus as recited in claim 13 wherein said electrodes are formed of platinum wire.

17. The apparatus as recited in claim 13 wherein said electrodes are formed of silver/silver chloride wire.

18. In a feeding tube of the type having distal and proximal ends, a bolus at its distal end with an exit port means for supplying nutrients and a Y-connector at its proximal end, apparatus for determining the location of said bolus in and/or changes in the functioning of different areas of the gastrointestinal tract, said apparatus comprising, means provided on said bolus for detecting myoelectric signals developed by the surrounding area of the gastrointestinal tract in which it is located, and means for monitoring said signals for the benefit of an observer and/or for controlling a feeding system.

* * * * *